United States Patent
Squicciarini

(10) Patent No.: US 7,201,874 B2
(45) Date of Patent: Apr. 10, 2007

(54) SYSTEM FOR AUTOMATICALLY EXTRACTING AND ANALYZING RESIDUAL SOLVENTS IN MATERIAL SAMPLES

(76) Inventor: Carlo Squicciarini, Villa Raverio, Viale Kennedy, 98, Besana Brianza (IT) I-20045

( * ) Notice: Subject to any disclaimer, the term of this patent is extended or adjusted under 35 U.S.C. 154(b) by 279 days.

(21) Appl. No.: 10/239,434

(22) PCT Filed: Mar. 14, 2001

(86) PCT No.: PCT/EP01/02960

§ 371 (c)(1),
(2), (4) Date: Sep. 20, 2002

(87) PCT Pub. No.: WO01/71310

PCT Pub. Date: Sep. 27, 2001

(65) Prior Publication Data

US 2003/0021731 A1 Jan. 30, 2003

(30) Foreign Application Priority Data

Mar. 20, 2000 (EP) .................................. 00830204

(51) Int. Cl.
*G01N 33/44* (2006.01)
*G01N 30/00* (2006.01)
*G01N 1/22* (2006.01)
*G01N 1/24* (2006.01)

(52) U.S. Cl. .......................... 422/62; 422/68.1; 422/80; 422/88; 422/89; 422/90; 422/91; 422/92; 422/102; 422/103; 436/31; 436/32; 436/55; 436/85; 436/161; 436/177; 436/181

(58) Field of Classification Search .................. 422/62, 422/68.1, 80, 88–92, 102–104; 436/31–32, 436/55, 85, 161, 177, 181
See application file for complete search history.

(56) References Cited

U.S. PATENT DOCUMENTS 3,249,403 A * 5/1966 Bochinski et al. ............ 422/89

(Continued)

FOREIGN PATENT DOCUMENTS

CS 150860 * 9/1973

OTHER PUBLICATIONS

Jeffs, A. R. Analyst 1969, 94, 249-258.*

(Continued)

*Primary Examiner*—Arlen Soderquist
(74) *Attorney, Agent, or Firm*—Mayer & Williams PC; Mark D. Wieczorek, Esq.

(57) ABSTRACT

A system for quickly and automatically extracting and analysing residual solvents is realised for operating directly in the premises where the packing materials are being manufactured, printed and/or laminated.

The system provides for a single unit equipped with a display and a keyboard, and comprises an extraction (desorption) chamber (1), an analysis chamber with valves and separating columns, a detection system (17), and a data processing system (19).

The extracting or desorption chamber comprises a desorption cell (1) for receiving a vial (36; 37) containing said sample, and means are provided to keep the inside of said cell (1) at a pressure higher that that of the surrounding environment until a new sample has been introduced into the cell, thus accomplishing a "washing" of cell for eliminating polluting solvents coming from the desorption of a preceding sample and/or solvents present in the surrounding environment.

7 Claims, 4 Drawing Sheets

U.S. PATENT DOCUMENTS

| | | | | |
|---|---|---|---|---|
| 3,850,040 | A | * | 11/1974 | Orr et al. .................... 73/865.5 |
| 4,245,494 | A | * | 1/1981 | Legendre et al. ........... 73/19.02 |
| 4,532,320 | A | * | 7/1985 | Denzinger et al. ........... 528/498 |
| 4,541,268 | A | * | 9/1985 | Odernheimer ............. 73/31.07 |
| 4,627,221 | A | * | 12/1986 | Buchner ...................... 53/425 |
| 4,865,996 | A | * | 9/1989 | Castleman et al. .......... 436/161 |
| 4,973,434 | A | * | 11/1990 | Sirkar et al. .................... 264/4 |
| 5,039,489 | A | * | 8/1991 | Gleaves et al. ............ 422/68.1 |
| 5,065,614 | A | * | 11/1991 | Hartman et al. ........... 73/23.35 |
| 5,191,211 | A | * | 3/1993 | Gorman, Jr. ................. 250/282 |
| 5,313,061 | A | * | 5/1994 | Drew et al. ................. 250/281 |
| 5,741,959 | A | * | 4/1998 | Garcia et al. .............. 73/19.05 |
| 5,970,804 | A | * | 10/1999 | Robbat, Jr. .............. 73/863.12 |

OTHER PUBLICATIONS

Hagman, A. et al, Journal of Chromatography 1987, 395, 271-279.*

Long, J. W. et al, Journal of Chromatography 1988, 450, 394-398.*

Urakami, K. et al, Chemical & Pharamaceutical Bulletin 2000, 48, 1894-1897.*

Tsao, M. U. et al, Journal of Clinical and Laboratory Medicine 1964, 63, 1041-1053.*

Pausch, J. B. et al, The Journal of Automatic Chemistry 1978, 1, 22-27.*

Bicchi, C. et al, Farmaco, Edizione Pratica 1982, 37, 88-97.*

Jacobsson, S., Journal of High Resolution Chromatography and Chromatography Communications 1984, 7, 185-190.*

Sahlestrom, Y. et al, Analytica Chimica Acta 1986, 185, 259-269.*

Schmidt, S. et al, Journal of High Resolution Chromatography and Chromatography Communications 1988, 11, 242-247.*

Tsuge, S. et al, Journal of High Resolution Chromatography 1989, 12, 727-731.*

Takigawa, D. Y., Separation Science and Technology 1992, 27, 325-339.*

Manura, J. J. et al, American Laboratory 1992, 24, 46-52.*

Desobry, S. et al, Special Publication—Royal Society of Chemistry 1995, 162, 146-151.*

* cited by examiner

SYSTEM FOR AUTOMATICALLY EXTRACTING AND ANALYZING RESIDUAL SOLVENTS IN MATERIAL SAMPLES

BACKGROUND AND SUMMARY OF THE INVENTION

This invention relates to a system for quickly and automatically extracting and analysing residual solvents in material samples. Hereinbelow reference will be made particularly to preferred embodiments of the invention in which the samples are printed and/or laminated films, in general used as base supports for packing or packaging foodstuffs or pharmaceutical products, or liquid samples. Nevertheless, this is not to be understood as a limitation since the invention has several different applications, such as the analysis of residual monomers in polymers, the analysis of contaminated grounds, waters, and so on.

More particularly, the invention can be advantageously employed directly in the premises or plants where the materials for packing foodstuff and pharmaceutical products are being manufactured or printed and/or laminated.

As it is known the analyses of residual solvents present in printed and/or laminated packing materials, particularly those for packing foodstuffs and pharmaceutical products, are very important for the companies of this field.

According to a prior art technique, the analysis of residual solvents, for example in a film of plastic material, is carried out in laboratories by using an analytical system comprising a head-space sample container or thermal desorber, coupled to a gas chromatograph. During the manufacturing of the printed and/or laminated support or at the end of such process, a sample is collected and sent to the laboratory. The analysis results from the laboratory are available after times that are not compatible with the manufacturing schedules. Besides the high costs, the non-availability in real time of the analysis results often brings to discard large amounts of product and to reprocess the materials with additional costs.

This analysis is quite complex and requires high qualified technical personnel, and further has the following drawbacks:

the handling of the samples from the manufacturing plant to the analysis laboratory,
the use of test tubes, envelopes or other closed containers for transferring the samples to the laboratory with the associated risks of polluting the container content by the environment air, for example the air of the manufacturing plant when collecting the sample;
extremely complicated calibration procedures and frequent calibration controls, particularly for systems carrying out a subdivision or splattering of the sample;
long analysis times of the order of 45–60 minutes.

A further trouble of the known systems comes from the need to provide a pressure source and a gauge, which nevertheless does not allow a real knowledge of the pressure inside of the desorption chamber.

The scope of this invention is to eliminate the drawbacks and the limitations of the known systems, and more particularly to maintaining a higher pressure (overpressure) inside the desorption cell until a sample is introduced thereinto. By providing such overpressure or "washing" of the cell, it is possible to eliminate any pollutants coming from the desorption of a preceding sample and/or from the surrounding environment, whereby the system is suitable to be employed in the field still supplying reliable results. Preferably, the same fluid is used both as washing fluid and as fluid maintaining the high pressure, although this is not mandatory.

The above objects of this invention are achieved through a novel analyser for quickly analysing the residual solvent of a sample which analyser can be directly used in the sites where the packing article is being manufactured, printed and/or laminated.

The analyser according to the invention operates in a fully automatic manner and does not require highly trained personnel, reduces the handling of the samples to be analysed, and supplies results that are comparable with those obtainable in a laboratory by using the known procedures in times of the order of several minutes.

More particularly, for analysing printed and/or laminated packing articles, the system according to the invention can be advantageously located in the manufacturing premises, thus allowing for both the on-line analysing and the monitoring of the article being manufactured. As for what concerns the samples of packing materials, the invention allows to obtain the automatic analysis of solvent on both the sides of the sample, that is both on the outer side and on the inner side (that contacts the foodstuff or pharmaceutical product).

Moreover, the system according to the invention can operate on very small amounts of sample (the term "sample" being referred to the amount of the residual solvent) directly in the capillary column, thus eliminating sample splitting techniques that are subjected to introduce errors in the analysis.

According to the invention, these objects are achieved through a system for automatically extracting and analysing residual solvents in materials samples as described here.

BRIEF DESCRIPTION OF THE DRAWINGS

The invention will now be disclosed with particular reference to the attached drawings illustrating a non limiting embodiment thereof, in which.

Throughout all the Figures the same numerical references have been used to indicate equal or substantially similar parts.

DETAILED DESCRIPTION

Figure 1:
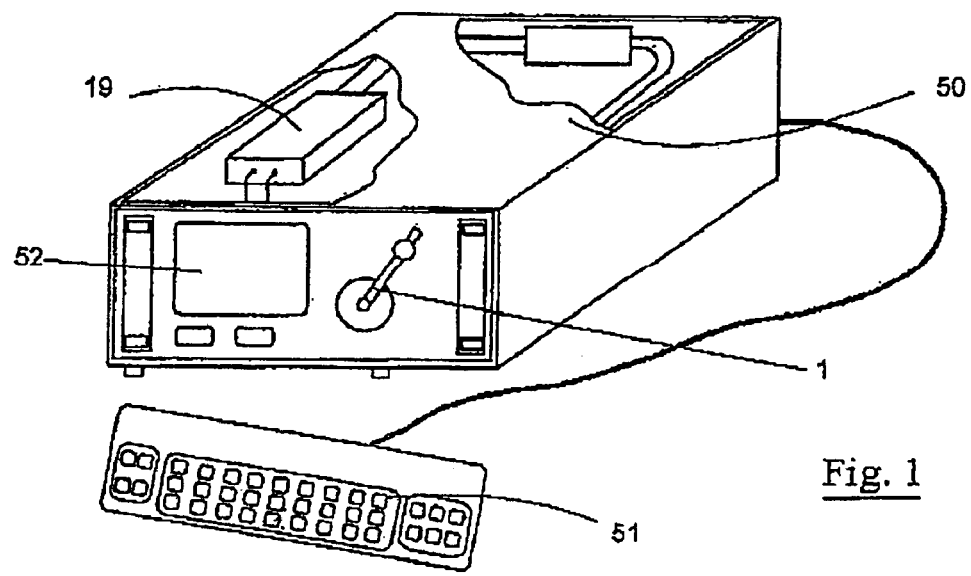
FIG. 1 is a schematic perspective view of an equipment implementing the system according to the invention.
Figure 2:
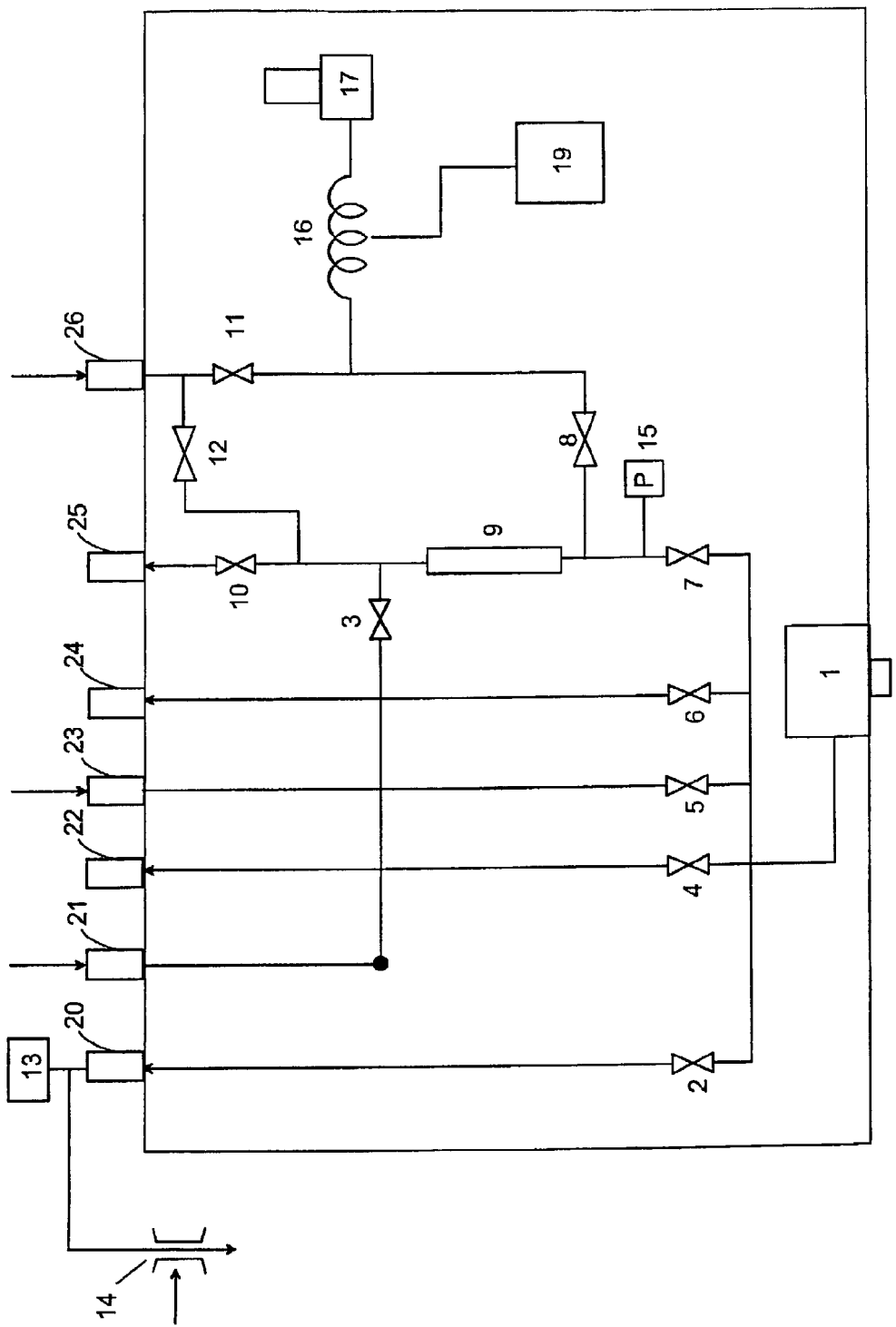
FIG. 2 is a general diagram of a system according to the invention.

With reference to FIGS. 1 and 2, a system according to the invention preferably comprises a single equipment piece disposed inside a container or thermostatic case 50, housing an analysis chamber equipped with valves and a separation column, and a data processing system. On the front panel of the equipment there are mounted an analysing or desorption cell 1, preferably kept at a fixed temperature, and a graphic display 52. A keyboard 51 for the controls is connected to the equipment, as well as a printer (not shown) to supply a hard copy of the analysis results.

The diagram of FIG. 2 illustrates with more details the components and the system operation. Such a system comprises a desorption cell 1 for extracting the solvents from a sample, that can be connected to a high resolution capillary column 16 in order to separate from one another the solvents present in the sample to be analysed. The column 16 is connected to a detection system 17, to a sampling loop 9, and to a processing and control unit 19. These components (as well as their modes of use) are known and however their functions could also be performed by different components so that they shall not be further described.

Additionally, means (not illustrated in the drawings) are provided for heating the sample and extract the solvents. Several fittings are provided for in the system for connecting this latter to the outside, such as:

a fitting 20 to be connected to a vacuum source;
a fitting 21 to be connected to a source of washing gas;
a fitting 22 for discharging the washing gas outside of the apparatus;
a fitting 23 to be connected to a pressure source;
a fitting 24 to be connected to a reference standard;
a fitting 26 for discharging the loop.

Moreover, a digital device 13 for controlling the vacuum level can be connected to the fitting 20, this device acting on a valve 14 (or other component) for adjusting the vacuum level, such valve being inserted in the connection between the fitting 20 and the vacuum source.

The fittings 20, 22, 23, 24 and 25 can be connected to the cell 1 through the corresponding valves 2, 4, 5, 6 and 7. The inlet of column 16 is connected to the fitting 26 through the valve 11, and to one end of loop 9 through the valve 8. The other end of loop 9 is connected to fitting 25 through a valve 10, to fitting 21 through a valve 3, and to fitting 26 through a valve 12.

A device 15 for controlling and adjusting the pressure is located between valves 7 and 8.

The cycle phases, the switching of the valves as well as other operations such as integrations, display of the chromatogram, data storage and so on, are under the control of unit 19, preferably realised through a PC located inside the analyser.

Figure 6:
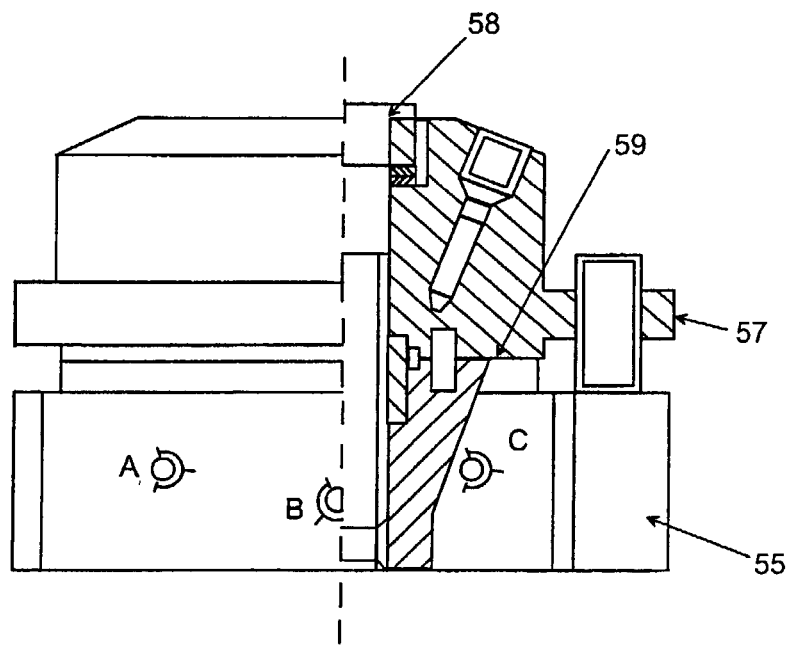
FIG. 6 schematically illustrates a preferred embodiment for realising some of the system valves through a single small volume automatic valve assembly.

Valves 2 to 6 are preferably realised as a monolithic (single) component comprising a single automatic valve assembly of small volume, schematically illustrated in FIG. 6, adapted to accomplish the required functions and installed into a thermostat system.

The valve 7, 8, 10, 11 and 12 realise an automatic valve assembly adapted to directly sample volumes from the capillary column and capable to sample a few microliters of sample without requiring special splitting techniques of the sample, thus eliminating the analysis errors inherent to such techniques.

Figure 3:
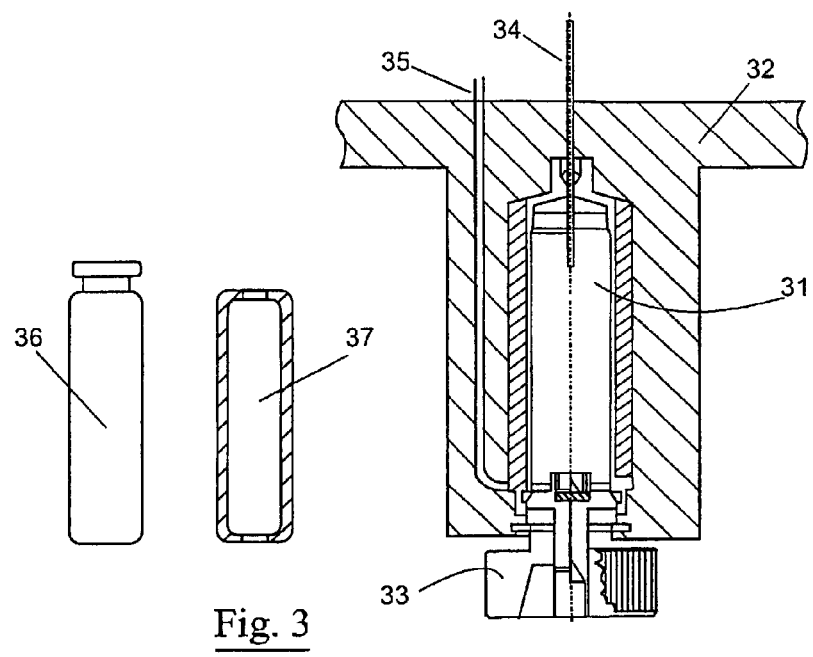
FIG. 3 is a cross section view illustrating with more details the desorption cell for a liquid or solid sample.
Figure 5:
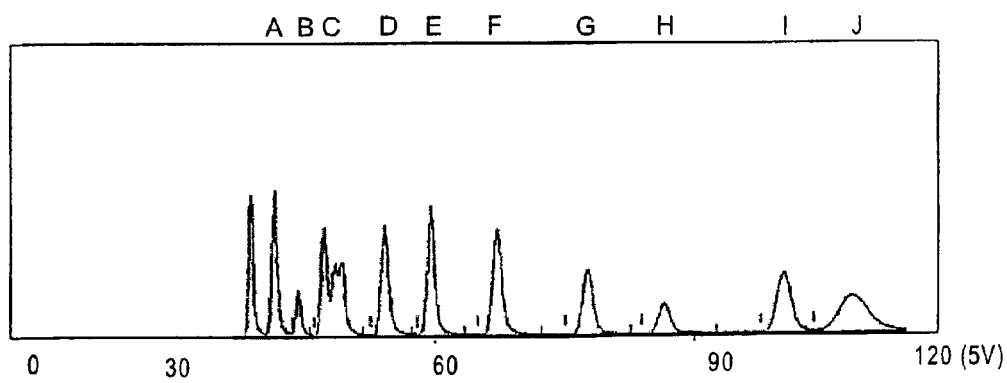
FIG. 5 shows an analysis diagram obtained by a system according to the invention.

With reference to FIG. 3 it will be illustrated an embodiment of a desorption cell which is adapted to be used with solid or liquid samples. Said desorption cell comprises a recess or seat 31 having a substantially cylindrical shape, formed in a properly insulated portion 32 of the equipment front panel and of a closing member or knob, 33 for sealingly closing the cell. A conduit 35, connected to the above mentioned valve 4 of the washing fitting 21 opens into the front portion of the cell and a needle 34 is located at the inner end of the cell.

The cell or seat 31 can receive test tubes or "vials" having a 20 cc capacity, said vials being either vials of the open type such as 37 or vials 36 for liquid or solid samples, that have been sealed through a ring carrying a pierceable septum. The thickness of the test tube or vial is such as the inner available volume of the cell is of 20 cc after the tube has been inserted into the seat.

After the introduction into the cell of a test tube closed by a septum 35, the closing knob 33 is screwed and sealingly tightened onto the test tube till the needle 34 perforates the septum.

Figure 4:
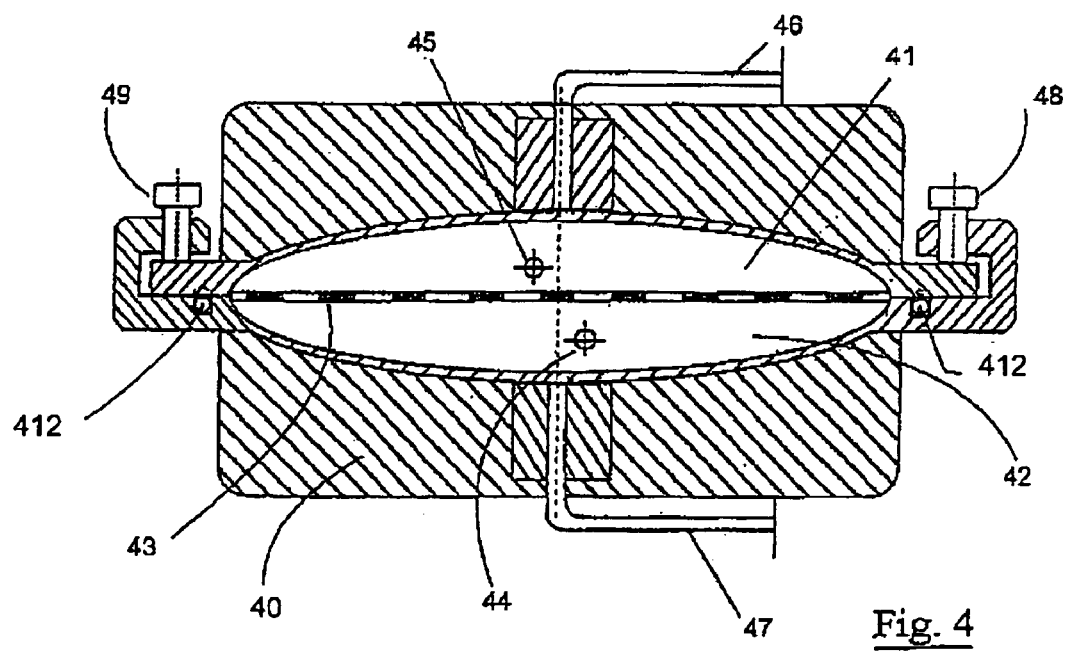
FIG. 4 is a cross section view illustrating with more details the desorption cell for a film or a support of packing materials.

FIG. 4 illustrates a cell adapted for analysing residual solvents in bases of printed and/or laminated packing for foodstuffs and pharmaceutical products, both on the outer and the inner surface of the packing sheet, this latter being the surface that will come in contact with the packed product. The cell comprises a recess divided by a net 43 for supporting the sample to be analysed, and forming two hollows 41 and 42, each one with a 20 cc volume. The recess is placed in an insulated volume 40 and the seal is ensured by at least one circular gaskets 412 fitting along the whole surface of hollow 42. Two conduits 46 and 47 for the connection to the washing and vacuum sources respectively, as well as two conduits 45 and 44 for the outlet of the vapour solvent, open in the hollows 41 and 42. Clamps 48 and 49 lock the cell into the correct position.

An analysis cycle of a system according to the invention will now be disclosed in detail.

Initially, a calibration cycle is carried out—wherein the desorption is not activated—by inserting into the desorption cell a mixture having a known concentration, such mixture being inserted either through a test tube or a vial closed by a pierceable septum, or by injecting the calibration mixture directly into the cell 1 by means of a syringe, through a pierceable septum.

A check of the calibration stability in the time can be carried out by using a reference standard by connecting to the fitting 24 a cylinder containing synthetic air with a known concentration of only one substance, such as for example methane. The reference calibration cycle is comparable with the cycle for analysing the sample and provides for a first analysis to store the value of methane area, and then a comparison of such value with a value that has been stored in subsequent reference calibration cycles.

For the real analysis, from an initial condition of standby, the valves 3, 7 and 4 are opened, whereby the desorption cell and the sampling loop, as well as the valve 11 for conveying a gas or "carrier" to the capillary column, are subjected to a washing.

Then the operator introduces the sample into the chamber 1 and starts the system, thus causing the closing the previously opened valves 3, 7 and 4, and the opening of valves 2 and 7 that apply the vacuum to the cell 1, to the loop 9 and to the valve 11, according to a predetermined cycle for a duration of a few minutes. During this cycle, the partial pressure is measured and monitored by the device 15 for controlling and adjusting the pressure.

The control of the partial pressure value inside the chamber during the sample desorption phase is very advantageous since it supplies an indication of the quantity of solvent desorbed (i.e. extracted) from sample. Of course, the value of such partial pressure shall be proportional to the amount of the desorbed solvent. Moreover this control allows for a later validation of the analysis results by verifying that the partial pressure value has always remained under the preset pressure value for the sample pressurization cycle.

Once the solvent desorption has occurred, that is when the solvent present in the sample has been converted to a gas in the cell, the valve 7 is opened again for communicating the sampling loop with the desorption cell 1 and the valve 11 with the capillary column.

The gaseous sample is therefore pressurised by opening the valves 5 and 7, respectively towards the pressurisation fitting 23 and the discharge 25 fitting, and the valve 11 of carrier to the capillary column. Through this pressurisation cycle a sufficient amount of gaseous sample to perform the analysis is achieved.

Then, the valves 7 and 10 are open to fill the loop with the gaseous sample and to bring the loop of the gaseous sample to the atmospheric pressure. Thereafter the valve 11 of the carrier is opened to the capillary column.

Then the gaseous sample is admitted into the gas chromatography column 16. By opening the valves 12 and 8 the carrier draws the gaseous sample from the sampling loop and introduces it into the analysis column. By using a quick capillary column, it is possible to obtain the separation of the solvents and the analysis printout and report in a time of about 2 minutes. At the end of the analysis cycle, the system comes back to the stand-by conditions.

The cycle of the reference standard is carried out after the calibration cycle and is identical to the analysis cycle but for the opening of the valve 6 after the sample has been introduced, by introducing the sample without the vacuum cycle. The system stores the response signal of the reference standard and checks its reproducibility in the time, by comparing the data obtained with those stored: as long as this value is reproducible, the system is properly calibrated.

Figure 2A:
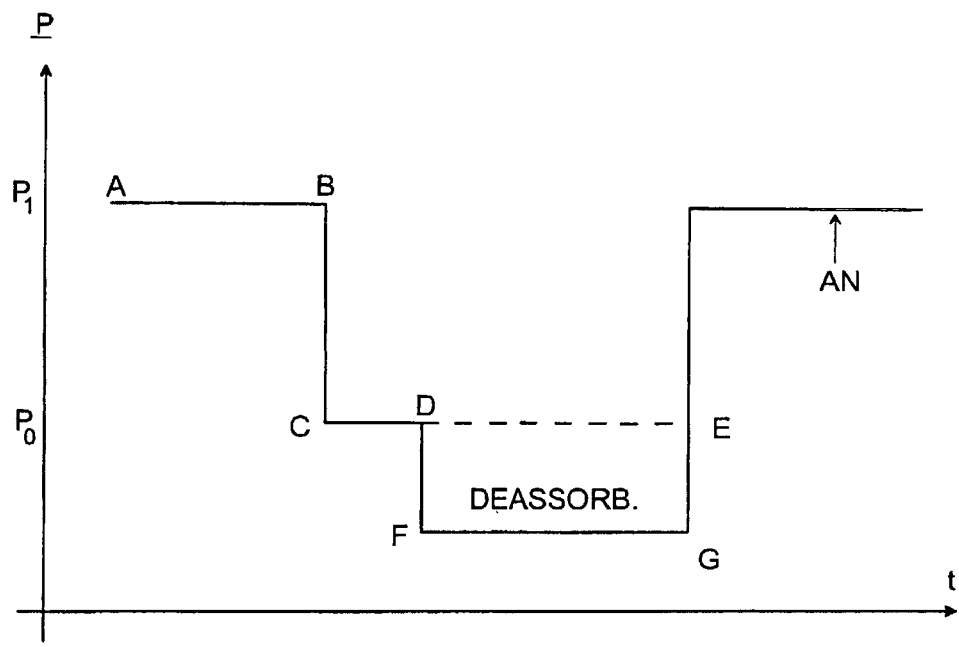
FIG. 2A schematically illustrates some steps of the method according to the invention.

FIG. 2A shows the values P of the pressure in the desorption cell as a function of time t. The AB section at a pressure p1 higher than the atmospheric pressure corresponds to the washing phase in which the gas keeps the cell at a pressure higher than the environment pressure to prevent the inlet of polluting solvents deriving either from the desorption of a previous sample or from the environment air containing solvents. The analysis starts at time AN.

At the beginning of the operations, the connection with the source of high pressure is closed and the pressure in the cell drops to the atmospheric value (p0) in the CD portion, the cell is then opened and the sample to be analysed is introduced in the cell. If the test tube is of the closed type, the needle 34 perforates the closing. During the desorption phase (in which the sample is being heated), the pressure can be kept either at the atmospheric level (as shown by the DE portion), or to a lower value (as shown by the FG portion) by connecting the chamber to the vacuum source. At the end of the desorption, the pressure is raised again to p1 level and the analysis cycle starts.

The valve assembly shown in FIG. 6 comprises a body 55 and a head 57 joined by a screw 58 with a diaphragm 59 interposed between the parts.

Although the invention has been illustrated with reference to preferred embodiments, it is generally susceptible of further applications and modifications that fall within the invention scope as will be evident to the skilled of the art.

The invention claimed is:

1. A system for automatically extracting and analysing the content of residual solvents in solid material samples, comprising:
   means for heating a sample in order to desorb or extract a solvent and comprising a desorption cell adapted to receive a vial having an opening at both ends and containing said sample;
   an analysis chamber with a separation column to separate components to be analysed;
   a plurality of valves for moving fluids inside said system;
   a detection system to identify the solvents;
   a control unit for controlling said plurality of valves and processing data;
   a casing kept at a predetermined temperature housing a part of said components;
   wherein said system further comprises
      a washing fluid source using a determined fluid for washing said cell and said open vial, and being connected to a washing valve;
      a pressure fluid source using said determined fluid for maintaining said cell and said open vial at a pressure higher than the atmospheric pressure, and being connected to a pressure valve;
      a vacuum source for maintaining said cell and said open vial at a pressure lower than the atmospheric pressure, and being connected to a vacuum valve;
      a pressure control device connected to said washing fluid source, to said pressure fluid source and to said vacuum source through the respective valves and configured for measuring, monitoring, and controlling the pressure inside said cell and said open vial;
      said pressure control device being arranged for measuring, monitoring, and controlling inside said cell at least three pressure levels:
         a pressure higher than the atmospheric pressure to wash said cell and said vial, and prevent the admission into said cell and said open vial of solvents from the surrounding environment;
         a pressure substantially equal to the atmospheric pressure to introduce the sample in the open vial and in the cell;
         a pressure lower than the atmospheric pressure to desorb said solid material samples;
      said control unit being arranged for controlling opening and closing of said respective washing valve, pressure valve and vacuum valve.

2. A system as claimed in claim 1, further comprising a one-piece valve assembly incorporating at least said pressure valve and said vacuum valve.

3. A system as claimed in claim 1, wherein said control unit is configured for maintaining said desorption cell a predetermined temperature.

4. A system as claimed in claim 1, wherein said analysis chamber comprises a capillary column adapted to separate the solvents present in the sample to be analysed, the capillary column being connected to a detection system, to a sampling loop, and to said control unit, and to a plurality of fittings for the outside connections including a fitting to be connected to a vacuum source, a fitting to be connected to said washing fluid source, a discharge fitting for the washing fluid, a fitting to be connected to said pressure fluid source, a fitting for a reference standard, and a loop discharge fitting.

5. A system as claimed in claim 1, further comprising a keyboard.

6. A system for automatically extracting and analysing the content of residual solvents in solid material samples, comprising:
   means for heating a sample in order to desorb or extract a solvent and comprising a desorption cell for containing said sample;
   an analysis chamber with a separation column to separate components to be analysed;
   a detection system to identify the solvents;
   a plurality of valves for moving fluids inside said system;

a control unit for controlling said plurality of valves and processing data;
a casing kept at a predetermined temperature housing a part of said components;
wherein said cell comprises
a recess having two hollows of equal volumes and being placed in a thermally insulated space, and
a net interposed between said two hollows for supporting the sample to be analysed,
said hollows comprising
respective outlet conduits connected to said analysis chamber for the outlet of the desorbed sample, and
respective inlet conduits connected to inlet conduits for washing said cell and for reducing the pressure therein,
said cell allowing the analysis of residual solvents in printed or laminated packing materials for packing or packaging foodstuffs and pharmaceutical products, both on the outer side and on the inner side in contact with the packed article.

7. A system as claimed in claim 6 further comprising a sealing circular gasket inserted along the whole surface of one of said hollows.

* * * * *